United States Patent [19]

Drabek

[11] Patent Number: 4,760,076
[45] Date of Patent: Jul. 26, 1988

[54] BENZISOTHIAZOLE DERIVATIVES AND THEIR USE AS INSECTICIDES

[75] Inventor: Jozef Drabek, Oberwill, Switzerland

[73] Assignee: Ciba-Geigy Corporation, Ardsley, N.Y.

[21] Appl. No.: 8,137

[22] Filed: Jan. 21, 1987

Related U.S. Application Data

[63] Continuation of Ser. No. 551,766, Nov. 14, 1983, abandoned.

[30] Foreign Application Priority Data

Nov. 26, 1982 [CH] Switzerland .......................... 6893/82
Oct. 12, 1983 [CH] Switzerland .......................... 5568/83

[51] Int. Cl.$^4$ .................... A01N 43/80; C07D 275/06
[52] U.S. Cl. ...................................... 514/373; 548/212
[58] Field of Search ............... 548/207, 212, 213, 214; 514/373

[56] References Cited

U.S. PATENT DOCUMENTS

| | | | |
|---|---|---|---|
| 3,562,283 | 2/1971 | Lewis et al. | 548/213 |
| 3,692,795 | 9/1972 | Boshagen | 548/212 |
| 3,707,364 | 12/1972 | Becke et al. | 548/207 |
| 3,849,430 | 11/1974 | Lewis et al. | 548/213 |
| 4,379,157 | 4/1983 | vanHes et al. | 548/207 |
| 4,698,358 | 10/1987 | Drabek | 514/373 |

FOREIGN PATENT DOCUMENTS

| | | | |
|---|---|---|---|
| 33984 | 8/1981 | European Pat. Off. | |
| 1960026 | 6/1971 | Fed. Rep. of Germany | 548/212 |
| 48-24735 | 7/1973 | Japan . | |
| 7324735 | 7/1973 | Japan | 548/212 |

Primary Examiner—Donald G. Daus
Assistant Examiner—Diana G. Rivers
Attorney, Agent, or Firm—Edward McC. Roberts; Kevin T. Mansfield

[57] ABSTRACT

The invention relates to the use of 3-acylaminobenzisothiazole-S,S-dioxides of the formula I

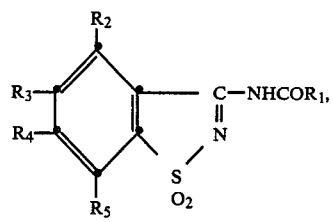

wherein $R_1$ is $C_1-C_{10}$alkyl, phenyl, or $C_1-C_{10}$alkyl which is substituted by halogen or $C_1-C_5$alkoxy, and $R_2$, $R_3$, $R_4$ and $R_5$ are each independently hydrogen, halogen, $C_1-C_5$alkyl, $C_1-C_5$alkoxy, trifluoromethyl, amino or nitro, for controlling insects and representatives of the order Acarina. The invention further relates to novel compounds of the formula I, wherein $R_1$ is $C_1-C_{10}$alkyl, phenyl, or $C_1-C_{10}$alkyl which is substituted by halogen or $C_1-C_5$alkoxy, and $R_2$, $R_3$, $R_4$ and $R_5$ are each independently hydrogen, halogen, $C_1-C_5$alkyl, $C_1-C_5$alkoxy, trifluoromethyl, amino or nitro, with the proviso that $R_2$, $R_3$, $R_4$ and $R_5$ are not at the same time hydrogen, as well as to the preparation of these compounds and to pesticidal compositions containing them.

25 Claims, No Drawings

BENZISOTHIAZOLE DERIVATIVES AND THEIR USE AS INSECTICIDES

This application is a continuation of application Ser. No. 551,766 filed 11-14-83.

The present invention relates to the use of 3-acylaminobenzisothiazole-S,S-dioxides for controlling insects and representatives of the order Acarina and to novel substituted 3-acylaminobenzisothiazole-S,S-dioxides, to the preparation thereof, and to compositions which contain these compounds.

In one of its aspects, the present invention relates to the use of 3-acylaminobenzisothiazole-S,S-dioxides of the formula I

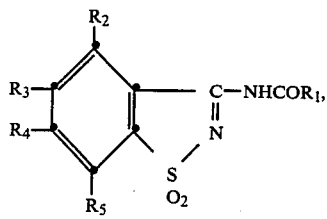

wherein $R_1$ is $C_1$–$C_{10}$alkyl, phenyl, or $C_1$–$C_{10}$alkyl which is substituted by halogen or $C_1$–$C_5$alkoxy, and $R_2$, $R_3$, $R_4$ and $R_5$ are each independently hydrogen, halogen, $C_1$–$C_5$alkyl, $C_1$–$C_5$alkoxy, trifluoromethyl, amino or nitro, for controlling insects and representatives of the order Acarina.

Within the scope of this invention, the compounds of formula I can also exist in their tautomeric form of the formula Ia

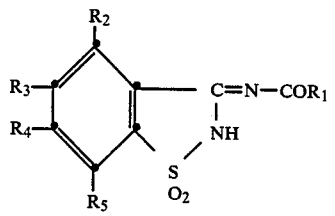

It is preferred to use compounds of the formula I, wherein $R_1$ is $C_1$–$C_{10}$alkyl, phenyl, or $C_1$–$C_{10}$alkyl which is substituted by fluorine, chlorine, bromine or $C_1$–$C_5$ alkoxy, and $R_2$, $R_3$, $R_4$ and $R_5$ are each independently hydrogen, fluorine, chlorine, bromine, $C_1$–$C_5$alkyl, $C_1$–$C_5$alkoxy, trifluoromethyl, amino or nitro, in particular those compounds of the formula I, wherein $R_1$ is $C_1$–$C_5$alkyl, preferably methyl, phenyl, or $C_1$–$C_3$alkyl which is substituted by 1 to 7 fluorine or chlorine atoms, $R_2$ is fluorine, chlorine, bromine, $C_1$–$C_5$alkyl, $C_1$–$C_5$alkoxy or trifluoromethyl, and $R_3$, $R_4$ and $R_5$ are each independently hydrogen, fluorine, chlorine, bromine, $C_1$–$C_3$alkyl, methoxy or trifluoromethyl.

On account of their insecticidal and acaricidal action, particularly interesting compounds of the formula I are those wherein $R_2$ is chlorine, $R_3$ is hydrogen or chlorine, and $R_4$ and $R_5$ are hydrogen.

In the definition of the compounds of the formula I mentioned above, halogen denotes fluorine, chlorine, bromine or iodine, with chlorine or fluorine being preferred. Suitable alkyl and alkoxy groups $R_1$ to $R_5$ may be straight chain or branched. Examples of alkoxy and unsubstituted or substituted alkyl groups $R_1$ to $R_5$ comprise: methyl, methoxy, —$CH_2Cl$, trifluoromethyl, ethyl, ethoxy, —$CH_2CH_2F$, —$CF_2CF_3$, propyl, —$CF_2$—$CF_2$—$CF_3$, isopropyl, n-butyl, isobutyl, sec-butyl and tert-butyl, n-pentyl, n-hexyl, n-decyl and the isomers thereof.

In another of its aspects, the present invention relates to novel compounds of the formula I, wherein $R_1$ is $C_1$–$C_{10}$alkyl, phenyl, or $C_1$–$C_{10}$alkyl which is substituted by halogen or $C_1$–$C_5$alkoxy, and $R_2$, $R_3$, $R_4$ and $R_5$ are each independently hydrogen, halogen, $C_1$–$C_5$alkyl, $C_1$–$C_5$alkoxy, trifluoromethyl, amino or nitro, with the proviso that $R_2$, $R_3$, $R_4$ and $R_5$ are not at the same time hydrogen.

Of the above mentioned novel compounds of the formula I, those compounds merit particular interest in which $R_1$ is $C_1$–$C_{10}$alkyl, phenyl, or $C_1$–$C_{10}$alkyl which is substituted by fluorine, chlorine, bromine or $C_1$–$C_5$alkoxy, and $R_2$, $R_3$, $R_4$ and $R_5$ are each independently hydrogen, fluorine, chlorine or bromine, $C_1$–$C_5$alkyl, $C_1$–$C_5$alkoxy, trifluoromethyl, amino or nitro, with the proviso that $R_2$, $R_3$, $R_4$ and $R_5$ are not at the same time hydrogen, as well as those compounds in which $R_1$ is $C_1$–$C_5$alkyl, phenyl, or $C_1$–$C_3$alkyl which is substituted by 1 to 7 fluorine or chlorine atoms, $R_2$ is fluorine, chlorine, bromine, $C_1$–$C_5$alkyl, $C_1$–$C_5$alkoxy or trifluoromethyl, and $R_3$, $R_4$ and $R_5$ are each independently hydrogen, fluorine, chlorine, bromine, $C_1$–$C_3$alkyl, methoxy or trifluoromethyl.

Particularly preferred on account of their excellent pesticidal, in particular aphicidal, action, are those novel compounds of the formula I, wherein $R_1$ is methyl and/or $R_2$ is chlorine, $R_3$ is hydrogen or chlorine and $R_4$ and $R_5$ are hydrogen.

Benzisothiazole-S,S-dioxides having fungicidal and bactericidal properties are already known from Japanese patent publication Sho 48-24735, wherein reference is also made generally, inter alia, to corresponding 3-acylamino derivatives containing a substituted fused benzene ring. Further, substituted 3-aminobenzisothiazole-S,S-dioxides having aphicidal properties are known from European patent application No. 0033984.

Surprisingly, it has now been found that the 3-acylaminobenisothiazole-S,S-dioxides of the formula I according to this invention are most effective insecticides, in particular aphicides. The above defined novel compounds of the formula I, wherein at least one of the radicals $R_2$, $R_3$, $R_4$ and $R_5$ has a meaning different from hydrogen within the given definition, have particularly good biological activity.

The above mentioned compounds of the formula I can be prepared in accordance with known methods (q.v. J. March, "Advanced Organic Chemistry", McGraw Hill, New York, 1977, pp. 383–385) by reacting a 3-aminobenzisothiazole-S,S-dioxide of the formula II

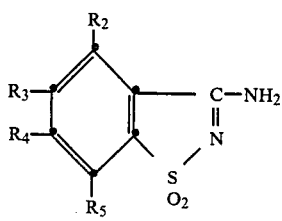

with an acid halide of the formula III $$X—COR_1 \quad (III)$$

or with an acid anhydride of the formula IV $$R_1OC—O—COR_1 \quad (IV)$$

optionally in the presence of a base, in which formulae II to IV above the radicals $R_1$ to $R_5$ are as defined for formula I and X is halogen, preferably chlorine.

Suitable bases are in particular tertiary amines such as trialkylamines, dialkylanilines and p-dialkylaminopyridines. The processes are carried out under normal pressure in the temperature range from $-25°$ to $150°$ C., preferably from $50°$ to $100°$ C., and optionally in a solvent or diluent.

Examples of suitable solvents or diluents are ethers and ethereal compounds such as diethyl ether, diisopropyl ether, dioxan and tetrahydrofuran; aromatic hydrocarbons such as benzene, toluene and xylenes; ketones such as acetone, methyl ethyl ketone and cyclohexanone; nitriles such as acetonitrile; esters such as ethyl acetate and butyl acetate; as well as dimethylformamide, dimethylsulfoxide, methyl cyanide and halogenated hydrocarbons.

Like the compounds of formula Ia, the compounds of formula II can also be in the form of their tautomers of the formula IIa

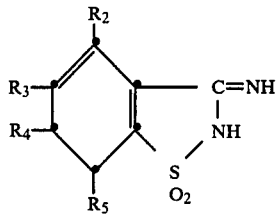
(IIa)

The starting materials of the formulae II, III and IV are known or they can be prepared by known methods. For example, the preparation of 3-aminobenzisothiazole-S,S-dioxides of the formula II is described in European patent application No. 0033984.

The compounds of formula I are suitable for controlling insects and representatives of the order Acarina in animals and plants. In addition, some of these compounds also have fungicidal and plant growth regulating properties.

In particular, the compounds of the formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as mites and ticks of the order Acarina.

Most particularly, the compounds of formula I are suitable for controlling plant-destructive insects, especially plant-destructive feeding insects, in ornamentals and crops of useful plants, especially in cotton, vegetable, rice and fruit crops. In this connection, particular attention is drawn to the fact that the compounds of formula I have both a strongly pronounced systemic and contact action against sucking insects, especially against sucking insects of the Aphididae family (e.g. against *Aphis fabae, Aphis cracciovora* and *Myzus persicae*), which can only be controlled with difficulty using known pesticides.

The compounds of formula I also have a useful action against feeding and biting insects as well as against flies, e.g. *Musca domestica,* and *mosquito larvae.*

Furthermore, the compounds of the formula I are suitable for controlling aectoparasites such as *Lucilia sericata* in domestic animals and productive livestock, e.g. by treating animals, cowsheds, barns, stables etc., and pastures.

The activity of the compounds of the formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, chlorinated hydrocarbons, and *Bacillus thuringiensis* preparations.

Compounds of formula I are also combined with particular advantage with substances which exert a pesticidally potentiating action. Examples of such compounds comprise: piperonyl butoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioate.

The good insecticidal activity of the proposed compounds of the formula I according to the invention corresponds to a mortality of at least 50–60% of the above insect pests.

The compounds of the formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}-C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8-C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8-C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi-(2-chloroethyl)-ethylammonium bromide.

The surfactants customarily employed in the art of formulation are described e.g. in "McCutcheon's Detergents and emulsifiers Annual", MC Publishing Corp. Ringwood, N.J., 1979.

The pesticidal compositions usually contain 0.1 to 99%, preferably 0.1 to 95%, of a compound of the formula I, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients in order to obtain special effects.

Formulation examples for solid active ingredients of the formula I (throughout, percentages are by weight)

| 1. Wettable powders | (a) | (b) | (c) |
|---|---|---|---|
| compound of formula I | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2. Dusts | (a) | (b) |
|---|---|---|
| compound of formula I | 5% | 8% |
| talcum | 95% | — |
| kaolin | — | 92% |

Ready for use dusts are obtained by mixing the active ingredient with the carriers, and grinding the mixture in a suitable mill.

| 3. Extruder granulate | |
|---|---|
| compound of formula I | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 4. Coated granulate | |
|---|---|
| compound of formula I | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 5. Suspension concentrate | |
|---|---|
| compound of formula I | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 1

Preparation of 3-chloroacetylaminobenzisothiazole-S,S-dioxide 12.75 g of 3-aminobenzisothiazole-S,S-dioxide and 50 g of chloroacetanhydride are stirred for 10 hours at 100° C. The reaction mixture is then poured into 1 liter of toluene. The precipitate is filtered with suction and washed on the filter with toluene and ether. The filter residue is dried in vacuo to give the title compound (compound 1) of the formula

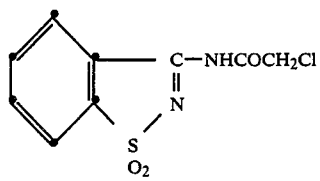

with a melting point of 183°–186° C.

EXAMPLE 2

Preparation of 3-acetylamino-4-chlorobenzisothiazole-S,S-dioxide 10.2 g of 3-amino-4-chlorobenzisothiazole-S,S-dioxide and 70 ml of aceticanhydride are stirred for 48 hours at 100° C. The reaction mixture is cooled and the precipitated crystals are filtered with suction, washed with water and dried at 80° C., affording yellow crystals of the title compound (compound 5) with a melting point of 210°–213° C.

The following compounds of the formula I are also prepared in corresponding manner:

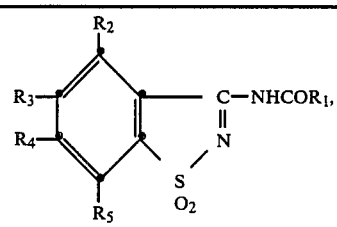

| No. | $R_1$ | $R_2$ | $R_3$ | $R_4$ | $R_5$ | Physical data |
|---|---|---|---|---|---|---|
| 2 | —$C_2H_5$ | H | H | H | H | m.p.: 233–236° C. |
| 3 | —$C_3H_7(n)$ | H | H | H | H | m.p.: 211–213° C. |

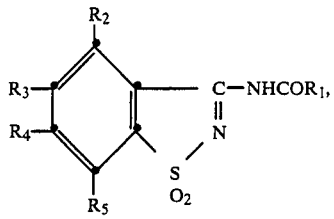

| No. | $R_1$ | $R_2$ | $R_3$ | $R_4$ | $R_5$ | Physical data |
|---|---|---|---|---|---|---|
| 4 | phenyl | H | H | H | H | m.p.: 230–235° C. |
| 5 | —$CH_3$ | Cl | H | H | H | m.p.: 210–213° C. |
| 6 | —$C_2H_5$ | Cl | H | H | H | m.p.: 176–178° C. |
| 7 | phenyl | Cl | H | H | H | m.p.: >250° C. |
| 8 | —$CH_3$ | H | H | H | H | m.p.: 264–265° C. |
| 9 | —$CH_2Cl$ | Cl | H | H | H | m.p.: 181–185° C. |
| 10 | —$CF_3$ | Cl | H | H | H | m.p.: 201–202° C. |
| 11 | —$C_3H_7(i)$ | Cl | H | H | H | m.p.: 187° C. |
| 12 | —$C_5H_{11}(n)$ | H | H | H | H | m.p.: 219–221° C. |
| 13 | —$C_5H_{11}(n)$ | Cl | H | H | H | m.p.: 120–123° C. |
| 14 | —$CF_2CF_2CF_3$ | H | H | H | H | m.p.: 189–192° C. |
| 15 | —$CF_2CF_2CF_3$ | Cl | H | H | H | m.p.: 245–246° C. |
| 16 | —$CF_2$—$CF_3$ | H | H | H | H | m.p.: 234–236° C. |
| 17 | —$CF_2$—$CF_3$ | Cl | H | H | H | m.p.: 241–242° C. |
| 18 | —$CCl_3$ | H | H | H | H | m.p.: 210–212° C. |
| 19 | —$CCl_3$ | Cl | H | H | H | m.p.: 244–247° C. |
| 20 | —$CF_3$ | H | H | H | H | m.p.: 236–238° C. |
| 21 | —$C_3H_7(i)$ | H | H | H | H | m.p.: 267–270° C. |
| 22 | —$CH_3$ | Cl | Br | H | H | m.p.: 225–230° C. |
| 23 | —$C_2H_5$ | Cl | Br | H | H | m.p.: 237–240° C. |
| 24 | —$CH_3$ | H | $CH_3$ | H | H | m.p.: 283–286° C. |
| 25 | —$C_3H_7(n)$ | Cl | H | H | H | m.p.: 186–188° C. |
| 26 | —$C_2H_5$ | Cl | H | H | Cl | m.p.: 240–143° C. |
| 27 | —$CH_3$ | Cl | H | H | Cl | m.p.: 235–238° C. |
| 28 | —$CH_3$ | H | H | Cl | H | m.p.: >260° C. |
| 29 | —$CH_3$ | H | H | H | Cl | m.p.: 245–248° C. |
| 30 | —$CH_3$ | $CH_3$ | H | H | H | m.p.: 242–245° C. |
| 31 | —$CH_3$ | F | H | H | H | m.p.: 209–212° C. |

The following compounds can also be prepared as described above:

| No. | $R_1$ | $R_2$ | $R_3$ | $R_4$ | $R_5$ |
|---|---|---|---|---|---|
| 32 | —$CH_3$ | H | Cl | H | —$OCH_3$ |
| 33 | —$CH_3$ | Cl | H | H | —$NO_2$ |
| 34 | —$CH_3$ | —$CH_3$ | H | —$CH_3$ | —$CH_3$ |

EXAMPLE 3

Insecticidal contact action against Aphis Craccivora

Before the start of the test, bean plants (*Vicia faba*) reared in pots are each populated with about 200 insects of the species *Aphis craccivora*. The treated plants are sprayed 24 hours later dripping wet with an aqueous formulation containing 0.75, 12.5, 50, 100, 200 and 400 ppm of the compound to be tested. Two plants are used for each test compound at its given concentration and a mortality count is made after a further 24 hours.

EXAMPLE 4

Insecticidal systemic action against Aphis craccivora

Bean plants which have grown roots are transplanted into pots containing 600 ccm of soil. Then 50 ml of a formulation prepared from a 25% wettable powder containing 0.75, 3, 12.5 or 50 ppm of the compound to be tested are poured direct onto the soil in the pots.

After 24 hours the parts of the plants above the soil are populated with lice of the species Aphis craccivora and a plastic cylinder is then slipped over the plants to protect the lice from any possible contact with the test substance either directly or via the gas phase. A mortality count is made 48 and 74 hours respectively after the start of the test. Two plants, each in a separate pot, are used for each test substance at its given concentration. The test is carried out at 25° C. and 70% relative humidity.

EXAMPLE 5

Insecticidal contact action against Myzus persicae

Pea plants which have been reared in water to a height of 4 cm are each populated with about 200 aphids of the species Myzus persicae before the start of the test. The treated plants are then sprayed dripping wet 24 hours later with an aqueous suspension containing the compound to be tested in a concentration of 50, 100 or 200 ppm. Two plants are used for each compound at its given concentration. A mortality count is made 48 hours after application. The test is carried out at 20°-22° C. and 60% relative humidity.

EXAMPLE 6

Insecticidal systemic action against Myzus persicae

Bean plants which have grown roots are transplanted in the 4- to 5-leaf stage into pots containing 600 ccm of soil. Then 50 ml of an aqueous formulation (prepared from a 25% wettable powder) of the compound to be tested, in a concentration of 0.75, 3 and 12.75 ppm are poured direct onto the soil.

After 24 hours the parts of the plants above the soil are populated with aphids of the species Myzus persicae and plastic cylinders are then slipped over the plants to protect the aphids from any possible contact with the test substance either directly or via the gas phase. A mortality count is made 48 hours after the start of the test. Two plants, each in a separate pot, are used for each test substance at its given concentration. The test is carried out at about 25° C. and 60% relative humidity.

EXAMPLE 7

Insecticidal leaf penetration action against Aphis craccivora

A small shoot of Vicia faba, which is highly infested with aphids of the species Aphis craccivora, is placed in each of a number of 8 cm high plastic beakers (diameter about 6 cm). Each beaker is covered with a plastic lid having a punched opening of 2 cm diameter in the centre. A leaf of a Vicia faba-plant is then placed over the opening in the lid without separating this leaf from the potted plant. The leaf is then fixed on the beaker with a second punched lid above the opening of the first lid. From underneath, i.e. through the opening of the first lid, the aphids in the beaker then infect the leaf of the plant used as bait. An aqueous formulation of the test compound is then applied in a concentration of 100 ppm uniformly with a brush to the top side of the leaf. An investigation is then made to determine whether the test substance applied to the top side of the leaf of the plant used as bait has diffused in sufficient amount through the leaf to its underside to kill aphids sucking thereon.

The test is carried out at about 20° C. and 60% relative humidity. The evaluation of percentage mortality is made 48 hours after application of the test compound.

Biological test results

The results of the tests carried out in the foregoing Examples 3 to 7 are reported in the table, using the following rating to indicate the percentage kill of the pests ("-" means "not tested"):

A: 80-100% kill at a concentration of 0.75 ppm
B: 80-100% kill at a concentration of 3.0 ppm
C: 80-100% kill at a concentration of 12.5 ppm
D: 80-100% kill at a concentration of 50 ppm
E: 80-100% kill at a concentration of 100 ppm
F: 80-100% kill at a concentration of 200 ppm
G: 80-100% kill at a concentration of 400 ppm

| Com- | Contact action | | Systemic action | | Leaf penetration action |
|---|---|---|---|---|---|
| pound | Myzus | Aphis | Myzus | Aphis | Aphis |
| 1 | D | E | B | C | E |
| 2 | — | E | C | C | — |
| 3 | F | F | — | C | — |
| 4 | F | F | — | C | — |
| 5 | E | C | B | B | E |
| 6 | E | D | B | B | — |
| 7 | F | F | B | C | — |
| 8 | — | F | B | C | — |
| 9 | F | D | B | B | E |
| 10 | — | G | C | C | E |
| 11 | E | F | A | A | E |
| 13 | D | D | B | A | E |
| 15 | E | G | B | B | E |
| 17 | D | G | A | C | E |
| 19 | D | G | A | A | E |
| 25 | D | A | B | D | E |

What is claimed is:

1. A method of controlling acarids which comprises contacting said acarids or the locus thereof with an acaricidally effective amount of a compound of the formula

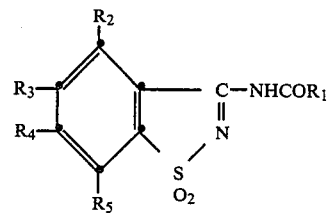

wherein $R_1$ is $C_1$-$C_5$alkyl, phenyl, or $C_1$-$C_3$alkyl which is substituted by 1 to 7 fluorine or chlorine atoms, $R_2$ is hydrogen, fluorine, chlorine, bromine, $C_1$-$C_5$alkyl, $C_1$-$C_5$alkoxy or trifluoromethyl, and $R_3$, $R_4$ and $R_5$ are each independently hydrogen, fluorine, chlorine, bromine, $C_1$-$C_3$alkyl, methoxy or trifluoromethyl, with the proviso that two or three of $R_2$, $R_3$ $R_4$ and $R_5$ are hydrogen.

2. The method of claim 1, wherein $R_1$ is methyl.

3. The method of claim 1, wherein $R_2$ is chlorine, $R_3$ is hydrogen or chlorine, and $R_4$ and $R_5$ are hydrogen.

4. The method of claim 3 wherein the compound is of the formula

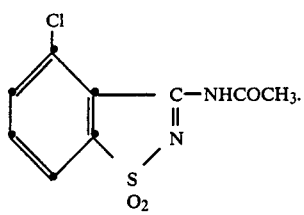

5. The method of claim 3 wherein the compound is of the formula

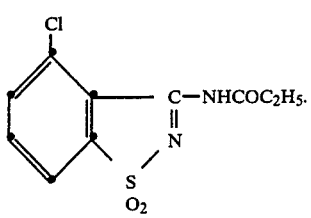

6. The method of claim 3 wherein the compound is of the formula

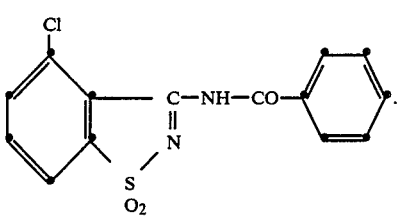

7. The method of claim 3 wherein the compound is of the formula

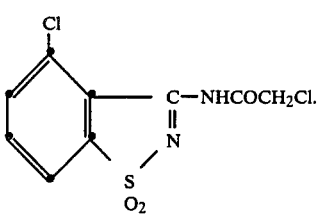

8. The method of claim 3 wherein the compound is of the formula

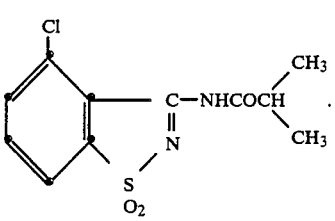

9. The method of claim 3 wherein the compound is of the formula

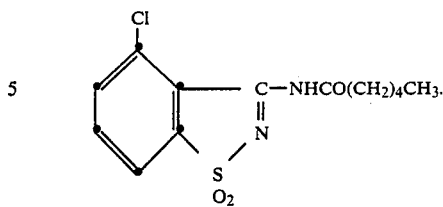

10. The method of claim 3 wherein the compound is of the formula

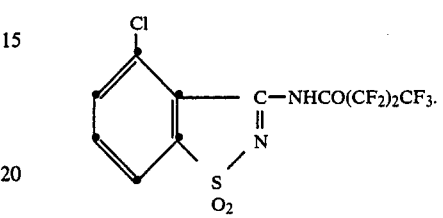

11. The method of claim 3 wherein the compound is of the formula

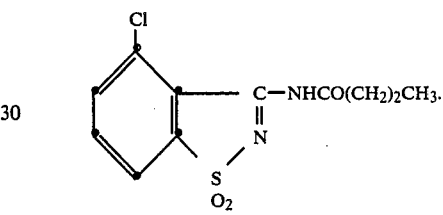

12. The method of claim 3 wherein the compound is of the formula

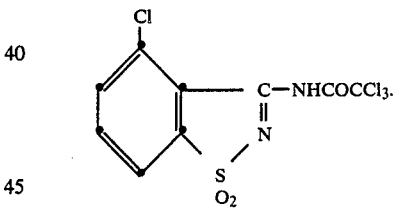

13. A compound of the formula

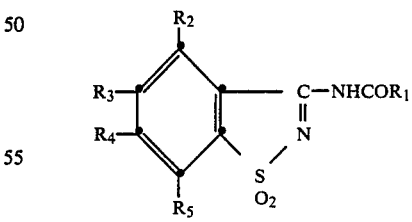

wherein $R_1$ is $C_1-C_5$alkyl, phenyl, or $C_1-C_3$alkyl which is substituted by 1 to 7 fluorine or chlorine atoms, $R_2$ is fluorine, chlorine, bromine, $C_1-C_5$alkyl, $C_1-C_5$alkoxy or trifluoromethyl, and $R_3$, $R_4$ and $R_5$ are each independently hydrogen, fluorine, chlorine, bromine, $C_1-C_3$alkyl, methoxy or trifluoromethyl, with the proviso that two or three of $R_3$, $R_4$ and $R_5$ are hydrogen.

14. A compound of claim 13, wherein $R_1$ is methyl.

15. A compound of claim 13, wherein $R_2$ is chlorine, $R_3$ is hydrogen or chlorine, and $R_4$ and $R_5$ are hydrogen.

16. A compound of claim 15, of the formula

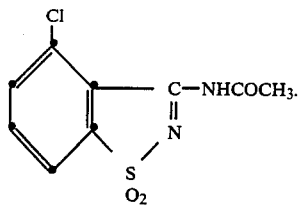

17. A compound of claim 15, of the formula

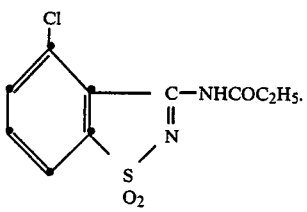

18. A compound of claim 15, of the formula

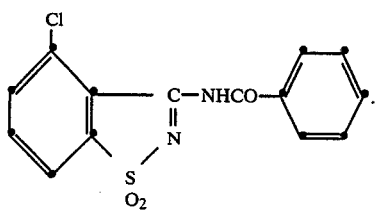

19. A compound of claim 15, of the formula

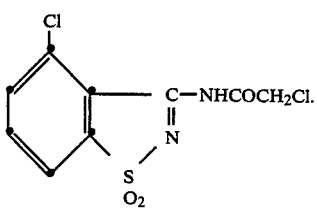

20. A compound of claim 15, of the formula

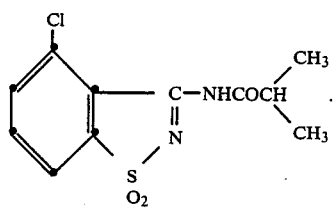

21. A compound of claim 15, of the formula

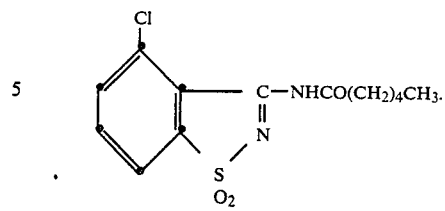

22. A compound of claim 15, of the formula

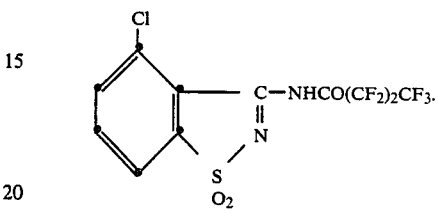

23. A compound of claim 15, of the formula

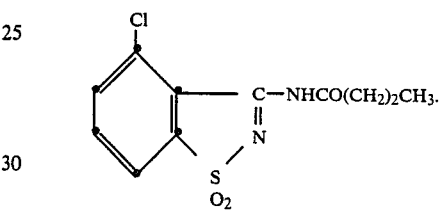

24. A compound of claim 15, of the formula

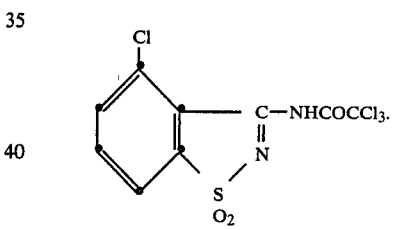

25. A pesticidal composition which contains as active ingredient a pesticidally effective amount of a compound of the formula

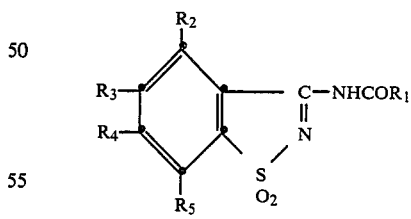

wherein $R_1$ is $C_1$-$C_5$alkyl, phenyl, or $C_1$-$C_3$alkyl which is substituted by 1 to 7 fluorine or chlorine atoms, $R_2$ is hydrogen, fluorine, chlorine, bromine, $C_1$-$C_5$alkyl, $C_1$-$C_3$alkoxy or trifluoromethyl with the proviso that two or three of $R_2$, $R_3$, $R_4$ and $R_5$ are hydrogen, together with a suitable carrier or other adjuvant.

* * * * *